United States Patent [19]

Tagliavini

[11] Patent Number: 4,682,601
[45] Date of Patent: Jul. 28, 1987

[54] ELECTRONIC DEVICE FOR CURATIVE STIMULATION OF THE BODY

[76] Inventor: Antonio Tagliavini, Via dei Canzi 26, Milano, Italy

[21] Appl. No.: 691,306

[22] Filed: Jan. 14, 1985

[30] Foreign Application Priority Data

Jan. 24, 1984 [IT] Italy .................. 20627/84[U]

[51] Int. Cl.[4] .............................................. A61N 1/36
[52] U.S. Cl. .................................. 128/422; 128/70; 128/796; 128/798
[58] Field of Search ................... 128/420 R, 421, 422, 128/423 R, 795, 796, 798, 800, 802

[56] References Cited

U.S. PATENT DOCUMENTS

| 309,897 | 12/1884 | Thurston | 128/795 |
| 450,577 | 4/1891 | Davis | 128/796 |
| 693,257 | 2/1902 | Gavigan | 128/802 |
| 3,127,895 | 4/1964 | Kendall et al. | 128/422 |
| 4,014,347 | 3/1977 | Halleck et al. | 128/422 |
| 4,210,151 | 7/1980 | Keller, Jr. | 128/421 |
| 4,240,437 | 12/1980 | Church | 128/421 |

Primary Examiner—William E. Kamm
Attorney, Agent, or Firm—Guido Modiano; Albert Josif

[57] ABSTRACT

A body stimulation electronic device is disclosed comprising an astable multivibrator for generating spike-like electric pulses, having a frequency up to 500 Hz, and, associated with the box-like enclosure housing the astable multivibrator, sockets for body stimulating electrodes and a potentiometer for adjusting the amplitudes of the produced pulses.

1 Claim, 3 Drawing Figures

ELECTRONIC DEVICE FOR CURATIVE STIMULATION OF THE BODY

BACKGROUND OF THE INVENTION

This invention relates to a portable electronic device for curative stimulation of the body.

It has become known for some time that treatment with electric or electomagnetic pulses is beneficial, in the medical field, to patients afflicted by either after-intervention traumas, atrophy, numbness, or other pains as due, for example, to ischemia or continued neuralgia, cervical ache, etc.

For this type of treatment, highly sophisticated and expensive electronic apparata have been developed and are available commercially which have generally proved satisfactory.

However, they are not devoid of problems, the main problem being that such apparata are not in general portable, thereby the patient is to go to a laboratory for application, while they can only be operated by highly skilled personnel.

SUMMARY OF THE INVENTION

In view of the above shortcomings, this invention is aimed at providing a portable electronic device for curative stimulation of the body, which is highly effective and can be manufactured as an apparatus for use and/or purchase by the individual user.

Within the above aim, it is a main object of the invention to provide a portable electronic device and/or apparatus for curative stimulation of the body which, additionally to being highly effective, may be manufactured from inexpensive electronic components, and can, therfore, br produced on a commercial scale at low production costs.

Another object of this invention is to provide a device as indicated, which can generate pulses which are readily adjustable frequency-and amplitude-wise and have current levels which are quite harmless to the patient.

A further object of the invention is to provide a device as indicated which may be equipped with stimulating electrodes of several types for stimulating different parts of the patient's body, which electrodes can be easily applied at locations of the device and/or apparatus pulse pick up, and may just as easily applied to the patient's body by the patient him/herself.

A not unimportant object of the invention is to provide a device and/or apparatus as indicated, which is truly effective to heed all of the affections previously mentioned and others yet, and which in no conditions of use constitutes a potential danger for the patient.

According to an object of the invention, the aim and objects mentioned above, and other objects yet, such as will be apparent hereinafter, are achieved by a portable electronic device for curative stimulation of the body which comprises, within a box-like enclosure, circuit means adapted to generate electric pulses, and associated with said box-like enclosure, sockets for stimulating electrodes and means for controlling the amplitudes of said pulses, characterized in that said pulses are very narrow, substantially spike-like pulses having a top frequency of 500 Hz.

BRIEF DESCRIPTION OF THE DRAWINGS

Further features and advantages of the electronic stimulating device according to the invention will be apparent from the following detailed description of an embodiment thereof, as illustrated by way of example only in the accompanying drawing, where.

DESCRIPTION OF THE PREFERRED EMBODIMENTS

Figure 1:
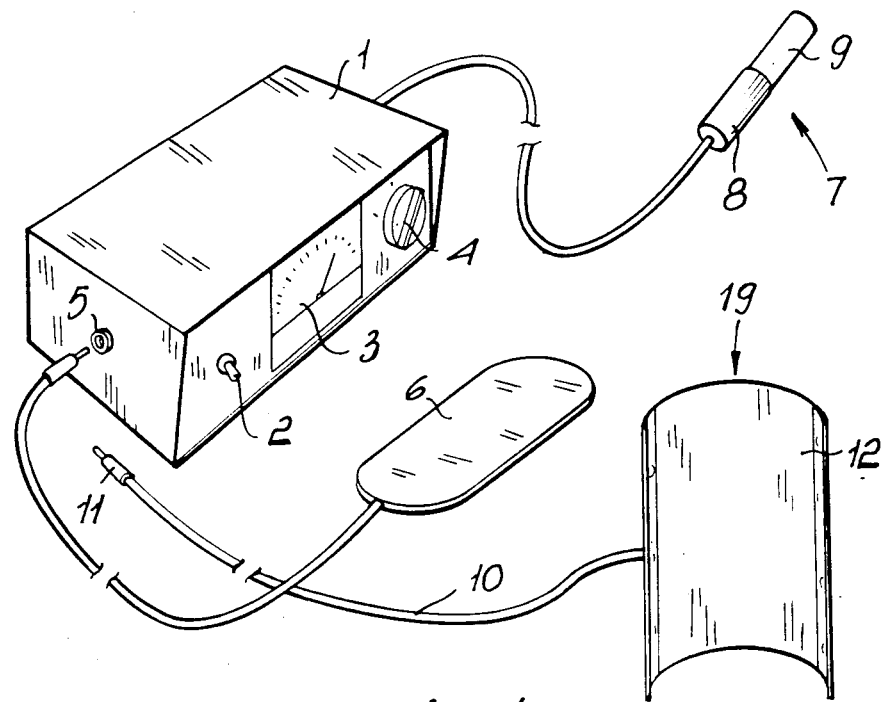
FIG. 1 is a perspective view of the general configuration of the stimulating device of this invention.

Making now more specific reference to the cited drawing figures, and particularly to FIG. 1, a device according to the invention comprises a box-like enclosure 1, the front panel whereof incorporates a switch 2, voltmeter 3, and adjusting knob 4, in particular a potentiometer knob.

At suitable locations on the side or rear/front panels the box-like enclosure 1 has sockets for picking up the pulses, the number whereof will depend on specific requirements. In particular, on a side panel of the box-like enclosure 1 there is indicated a socket 5 to which a first electrode, generally designated with the reference numeral 6, may be applied, for example, in the form of a metal shoe, in particular of aluminum, another socket, not specifically illustrated, being provided for connecting a stick element, generally designated with the reference numeral 7, having an insulating handgrip 8 and conducting metal portion 9 for stimulating the body part to be massaged. To that aim, it will be sufficient for the patient, after placing the shoe 6 under one of his/her feet, to run over the body part to be treated with the metal portion 9 of the stick while holding the stick 7 through the insulating handgrip 8.

According to another procedure, the patient also may, by gripping the metal portion 9 and again stepping on the aluminum shoe 6, rhythmically raise and lower the toes, thus feeling the heeding flow of the flowing current.

The inventive device may also have associated therewith, for example, another type of electrode, generally indicated at 19, comprising a lead wire 10 terminating in a pin 11 and a hose body 12 for adaptation for example to one arm.

Figure 2:
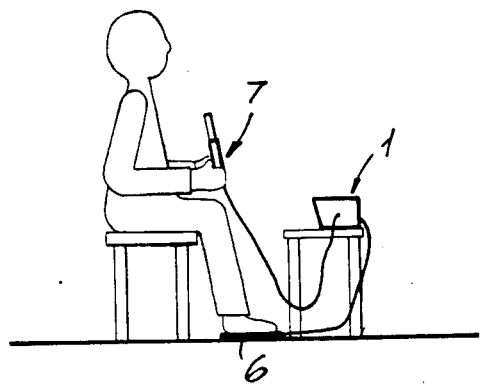
FIG. 2 is a diagramatic view illustrating the procedure for use of a device according to the invention by a patient.

With reference now to FIG. 2, illustrated therein is the procedure for use of the device according to the invention by the patient. As may be seen, that use is particularly simple, and the patient him/herself can, after providing for connection of the selected electrodes, effect the stimulating treatment of his/her own body parts requiring it. Of course, the patient shall have to be first trained by a physiotherapy doctor, or even just a nurse who may be familiar with the inventive device which is, however, quite simple to apply and can be mastered in a very short time.

According to the invention, the device produces spike or needle waves which have advantageously a frequency up to 500 Hz. The Applicant has found that this is the upper frequency limit that provides particularly effective results. In practice, in many treatments carried out, the device has been used up to 300–400 Hz and it has been observed that, when that limit is exceeded, the current becomes hardly bearable, unless a very thin nylon or cotton sock is worn on the foot which is to contact the shoe 6.

Figure 3:
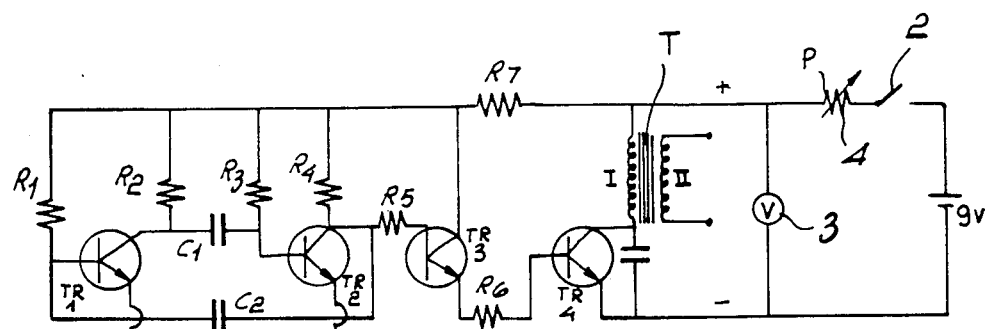
FIG. 3 shows an electronic circuit diagram as presently preferred for the production of the stimulating electric pulses, the circuit being associated with and forming an integral part of the device according to the invention.

For the production of the cited spike pulses, a very simple electronic circuit has been developed the general circuit diagram whereof is depicted in FIG. 3.

As may be seen, that electronic circuit comprises essentially a free-running multivibrator composed of the transistors $TR_1$, $TR_2$ and the various resistors interconnecting the transistor electrodes to the power supply provided by the common 9 Volt battery. In the diagram, $R_2$ and $C_1$ represent the time constant circuit of the free-running multivibrator, and although $R_2$ has been shown as including a fixed resistor, it may be a variable resistor for fine adjustment of the frequency of the pulses produced.

According to the invention, connected to the collector output of the transistor $TR_2$ is, through its base and a resistor $R_5$, a further transistor $TR_3$ which functions as a drive buffer, and the emitter whereof powers, through the resistor $R_6$, the base of the transistor $TR_4$ with final amplification function. The collector output of the transistor $TR_4$ is connected to the primary I of a transformer T the secondary II whereof reprsents the pulse pick up output for the electrodes which will always be referred to the negative or ground, indicated by "—", to which the shoe 6 will be connected.

A resistor $R_7$, connected at one end to the collector of the transistor $TR_3$ and at the other to one end of the primary I of the transformer T has the purpose of keeping the pulses produced perfectly stable, as has been ascertained with an oscilloscope check.

Together with the power supply, as may be seen, there is connected the potentiometer P(4) which is connected at its other end to the switch 2, the voltmeter 3 being interposed in the manner shown.

From tests carried out with the circuit illustrated it has been found that the pin waves produced by the combination of the transistors $TR_3$ and $TR_4$ are stable both at a minimum frequency advisably of 150 Hz and up to a frequency of 300 Hz and over, which has shown to be very effective for the patient heeding stimuli.

From an actually made sample the data shown in the following table have been gathered:

| INPUT VOLT | 2 | 3 | 5 | 7.5 hardly bearable |
|---|---|---|---|---|
| OUTPUT VOLT | 45 | 65 | 90 | 140 unless use is made of |
| HERTZ | 150 | 200 | 300 | 440 a nylon, or very thin cotton sock |

It may be seen from the foregoing that the invention fully achieves its objects. In particular, a body stimulating electronic device of the portable type has been provided which may be used by the patient at his/her home and is at the same time quite harmless, the current values supplied being on the order of milliamperes and quite far from potentially dangerous values.

The device is constructionally and circuitally simple, and as the skilled one will recognize, can be manufactured at competitive costs.

While the device of the invention has been described in connection with a presently preferred embodiment thereof, it should be held in mind that it is susceptible to many modifications and changes, all of which fall within the purview of the inventive concept. As an example, the number of the electrodes and their configuration may be any ones to fill individual requirements.

In practicing the invention, moreover, the materials and electronic components may be selected differently from those specifically shown, within the capability of the skilled one in the art.

I claim:

1. A portable electronic device for curative stimulation of the body, comprising a box-like enclosure; a free running multivibrator in said box-like enclosure for generating stimulating electric pulses, said free running multivibrator having a multivibrator output; a decoupling transistor connected to said multivibrator output and having a decoupling transistor output; an amplifier transistor connected to said decoupling transistor output and having an amplifier transistor output, a pulse transformer having a primary and a secondary, said pulse transformer primary being connected to said amplifier transistor output and said pulse transformer secondary having an output; said output of said pulse transformer secondary being coupled to sockets on said enclosure; electrode means to be coupled to said sockets for picking up said stimulating electric pulses; means for presetting the amplitudes of said stimulating electric pulses and for simultaneously presetting the frequencies thereof, said stimulating electric pulses having an amplitude which increases as the frequency thereof increases, the ratio of the value of said frequency in Hertz and of the value of said amplitude in volt being slightly greater than 3, the frequency range of said output pulses extending from 150 to 300 Hz and the amplitude range of said output pulses extending from 45 to 90 V.

* * * * *